United States Patent [19]

Lovalenti

[11] 4,249,075
[45] Feb. 3, 1981

[54] DETECTION OF BIRDSWING DEFECTS IN GLASS CONTAINERS

[75] Inventor: Sam Lovalenti, Toledo, Ohio

[73] Assignee: Owens-Illinois, Inc., Toledo, Ohio

[21] Appl. No.: 962,428

[22] Filed: Nov. 20, 1978

[51] Int. Cl.³ ............................................. G01N 21/51
[52] U.S. Cl. .................................. 250/223 B; 209/526; 356/240
[58] Field of Search ..................... 250/223 B; 356/240; 209/526

[56] References Cited

U.S. PATENT DOCUMENTS

| 2,753,459 | 7/1956 | Fedorchak | 250/223 B |
| 3,302,786 | 2/1967 | Conrad | 250/223 B |
| 3,328,000 | 6/1967 | Rottman | 250/223 B |
| 3,735,144 | 5/1973 | Babunovic et al. | 356/240 X |
| 3,894,806 | 7/1975 | Remy et al. | 250/223 B |
| 4,066,363 | 1/1978 | Juvinall | 356/240 X |

Primary Examiner—David C. Nelms
Assistant Examiner—Edward P. Westin
Attorney, Agent, or Firm—D. T. Innis; M. E. Click; D. H. Wilson

[57] ABSTRACT

Apparatus for inspecting glass containers to determine the presence of the defect termed "birdswing". A container under inspection is rotated and a laser is directed so as to pass through the opening defined by the finish of the container and toward the base of the container. If no birdswing is present the laser beam will pass through the bottom of the container. However, if a birdswing is present, the rotation of the container will cause the laser beam to eventually strike the birdswing, causing scattering of the laser beam. The scattered light is detected by a circumferential photocell array which is positioned below the base of the container. The location of the array is such that it will not detect any of the laser light unless it strikes a birdswing. The detection of scattered light by the photocell array causes a reject signal to be generated. As an alternative to rotation of the container, an electro-optical scanner may be employed to direct the laser beam through the opening of the finish of the container in a generally conical scan with respect to the axis of the container and thereby inspect a major portion of the interior space of the container.

1 Claim, 6 Drawing Figures

DETECTION OF BIRDSWING DEFECTS IN GLASS CONTAINERS

BACKGROUND OF THE INVENTION

One defect which occurs in the manufacture of glass containers is known as a "birdswing". This defect is a results of the two sides of the container contacting each other during the formation of the parison and prior to the blowing of the container into its final shape. The touching of the two sides of the container causes the hot glass to fuse together. As the container is blown to its final shape its sides that have touched will move away from each other drawing a small thread of glass therebetween, thus forming what is termed a birdswing. A birdswing need not consist of a complete thread running between the two inner walls of the container, as the thin filament of glass which would span the diameter of the container may break due to its becoming extremely thin and thereby cooling very rapidly, to the extent that it would break rather than stretch. However in every instance when a birdswing is formed, there will be small conical protruberances from the sidewalls in a direction of the opposite sidewalls, coincident with the formation of the birdswing.

One type of birdswing detector is disclosed in U.S. Pat. No. 3,438,492, issued to W. R. Albers on Apr. 15, 1969. A second system is disclosed in U.S. Pat. No. 3,662,883, issued to J. R. Sager on May 16, 1972. Both of these systems operate by passing a light beam through the wall of the container in order to detect the presence of a birdswing. Since other defects, such as checks, cracks or blisters might appear in the wall of the container, the accuracy of the above named systems may be impaired by these other types of defects being mistaken for birdswings. The present invention avoids this potential problem by passing a light beam which is used to inspect a container through the opening of the finish of the container rather than through the container wall. The light beam will thus strike a birdswing, if present, before passing through any other portion of the container.

SUMMARY OF THE INVENTION

This invention relates to the detection of birdswing defects in the interior of glass containers. A laser beam is projected through the opening defined by the finish of a container. If a birdswing is present, the laser beam will strike it and a light scattering pattern, made up of reflected and refracted light, will result. A circumferential array of photocells is positioned beneath the base of the container to detect light which is deflected from the birdswing. When deflected light is detected by the photocell array, a reject signal is generated by an electronic circuit connected to the photocell array.

Several methods may be used to optically scan the interior of the container. In one method, the light beam is passed through the opening of the finish of the container in a fixed direction, and the bottle is rotated so as to allow the entire interior space of the bottle to be scanned. In another method, the container is not rotated and an electro-optical scanner is utilized to direct the laser beam through the opening of the finish of the container and scan the interior space of the container. The detection of the deflected light may be accomplished from either above or below the container.

DETAILED DESCRIPTION OF THE DRAWINGS

Figure 1:
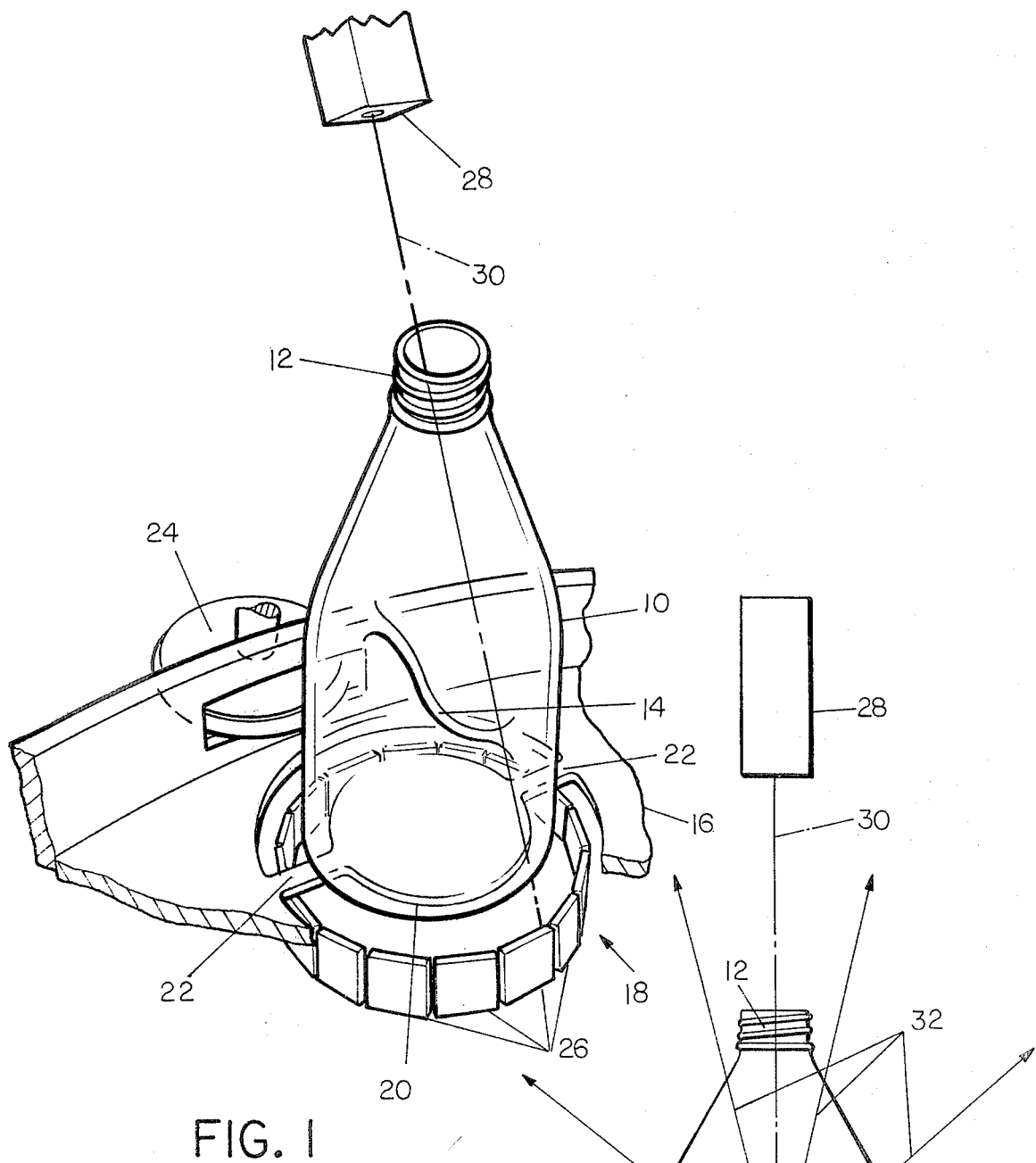
FIG. 1 is a perspective view of one embodiment of the invention showing a bottle in position to be inspected to determine whether or not a birdswing is present in the bottle.

Referring to FIG. 1 there is shown a glass bottle 10 having a finish area 12 and with an included birdswing defect 14. The bottle 10 moves along a plate 16 to an inspection area designated 18. While in the inspection area 18, the bottle 10 is supported on a circular base pad 20, which is connected to the plate 16 by two ribs 22. During inspection the bottle 10 is rotated on the base pad 20 by means of a drive wheel 24, which is conventional in the art. A star wheel or a pair of spaced rollers (not shown) on the opposite side of the bottle 10 with respect to the drive wheel 24 holds the bottle in place while it is rotated. One typical means of rotation is disclosed in U.S. Pat. No. 3,101,848, issued to A. F. Uhlig on Aug. 27, 1963, the disclosure of which is herein incorporated by reference. A circular photocell array 26 is located beneath the base pad 20 and receives light which is scattered from the birdswing 14. The photocell array 26 is generally coaxial with the base pad 20 and the bottle 10, and its diameter is somewhat larger than that of the bottle 10. A laser source 28 generates a laser beam 30 which is projected through the finish 12 of the bottle 10 and towards the base of the bottle 10. Although a laser is used, a finely focused beam of light other than laser light could also be utilized. As the bottle 10 rotates, the laser beam 30 will strike the birdswing 14 and a scattering pattern will result. Some of the light which is scattered will strike the photocell array 26. If the laser beam 30 does not strike the birdswing 14 (or if a birdswing is not present), the beam 30 will pass through the bottom of the bottle 10 and will not strike the photocell array 25. Thus, the presence of a birdswing 14 is determined by whether or not the photocell array 26 receives light from the laser 28.

Figure 2:
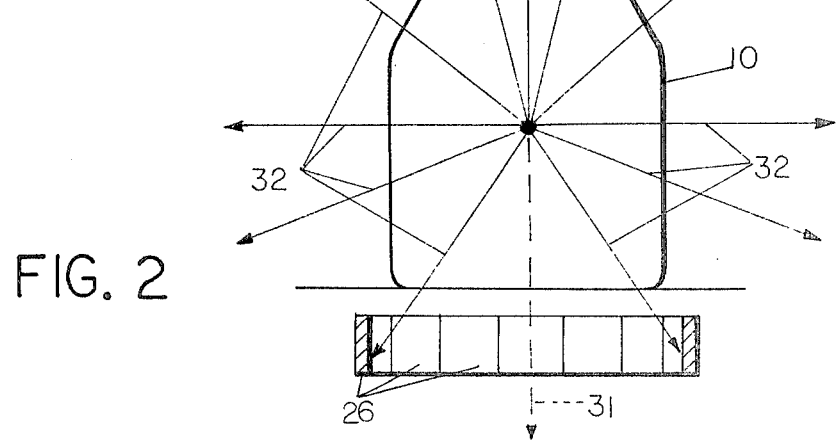
FIG. 2 is a schematic side elevational view partially in section, of the invention in relation to a bottle under inspection.

Referring now to FIG. 2, the scattering pattern which is created when the laser beam 30 strikes a birdswing 14 is shown. As shown by arrows 32, the beam 30 is scattered generally perpendicularly to the birdswing 14. The scattering is not limited to one particular direction, but rather encompasses a full 360° around the birdswing 14. Two of the deflected beams 32 which are shown strike the photocell array 26. If no birdswing were present the laser beam 30 would pass through the bottom of the bottle 10, as is shown by a dashed line 31. In such a case, no light from the beam 30 would strike the photocell array 26. Since the deflected rays 32 extend completely around the birdswing 14, the photocell array 26 need not necessarily be located beneath the bottle 10 as shown in the figure. The photocell array 26 would also receive deflected light if it were located above the bottle 10, and positioning of the array 26 below the bottle 10 is purely a matter of convenience.

Figure 3A:
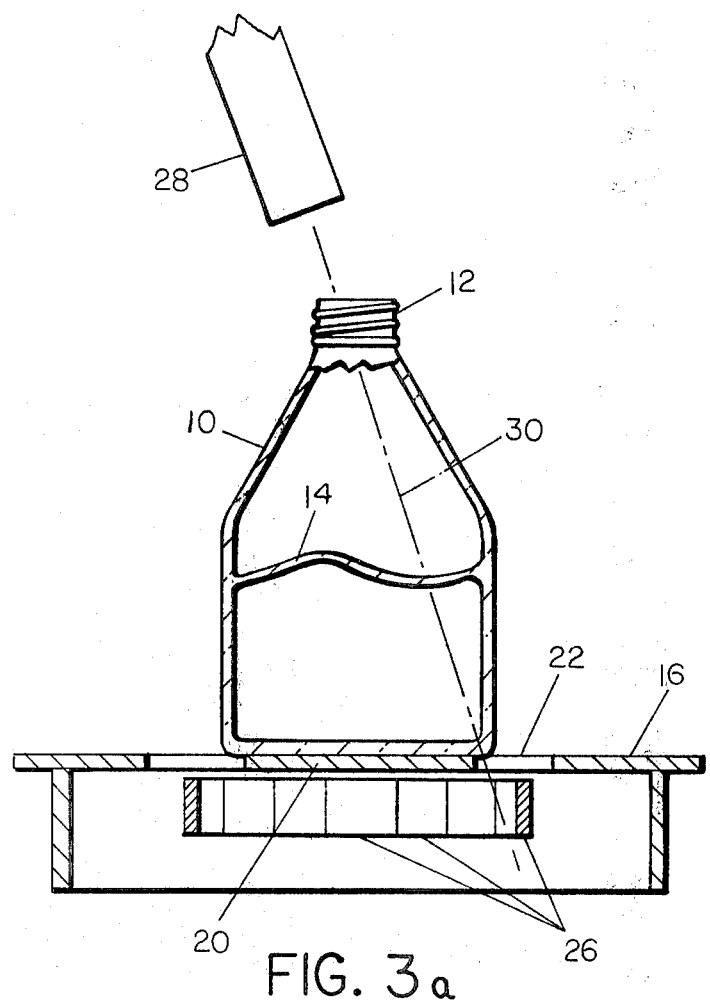
FIGS. 3A and 3B are side elevational view, partially in section, of the invention showing alternate orientations of a laser source which is utilized in the inspection of bottles.
Figure 3B:
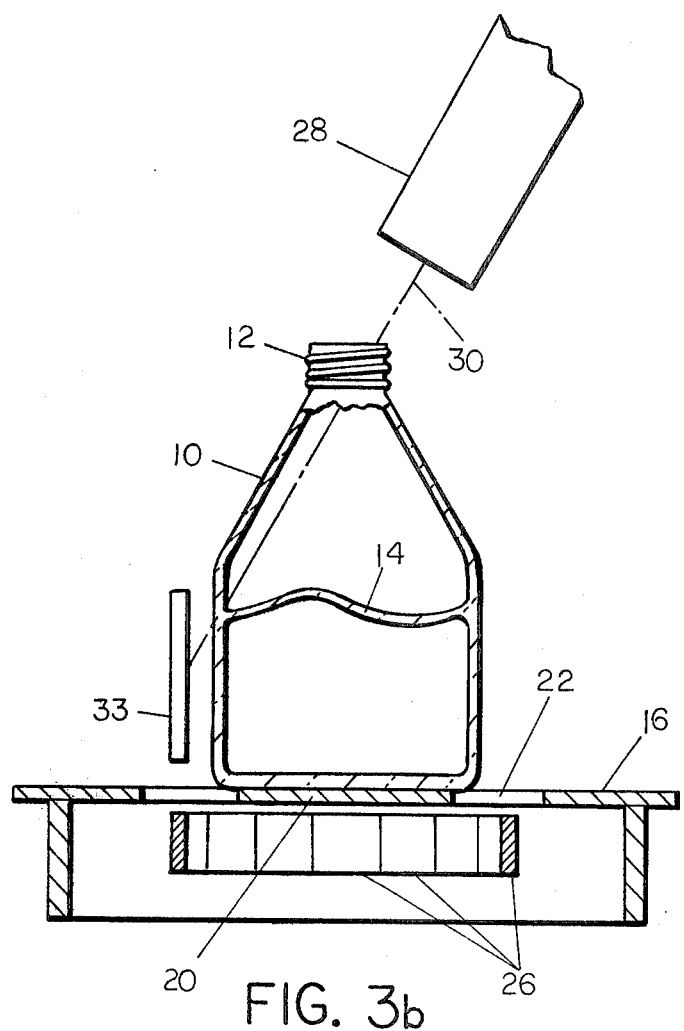

Referring now to FIGS. 3A and 3B, the laser 28 may be aimed so that it passes as close to the wall of the bottle 10 as is possible. This permits the detection of birdswings which may not be completely formed which would not be detected if the laser 28 were aimed straight through the center of the finish 12 so as to pass through the center of the interior space of the bottle 10. Depending upon the nature of the bottle under inspection, birdswings often appear above a particular point along the height of the bottle 10. If the entire height of the bottle 10 needs to be inspected, the laser 28 is aimed so as to strike the heel of the bottle 10, i.e., the intersection of the bottom of the bottle 10 and the wall of the bottle 10, as shown in FIG. 3A. If only the portion of the wall of the bottle 10 above a particular height need be inspected, the laser 28 may be aimed to strike the wall of the bottle 10, as shown in FIG. 3B, thus permitting the laser beam 30 to pass closer to the wall of the bottle 10 along its path. In such a case, the portion of the interior space of the bottle 10 below which the laser beam 30 strikes could not be inspected. If birdswings generally do not occur in this portion of the bottle 10, however, it may be worthwhile to project the laser beam 30 as close as possible to the wall of the bottle 10 in order to detect even the slightest protuberance caused by an incomplete birdswing. In order to prevent the laser beam 30 from striking the photocell array 26 directly, a vertical wall or mask 33 is positioned to intercept the beam 30 after it passes through the wall of the bottle 10. This insures that only light which is scattered after striking a birdswing will strike the photocell array 26.

Figure 4:
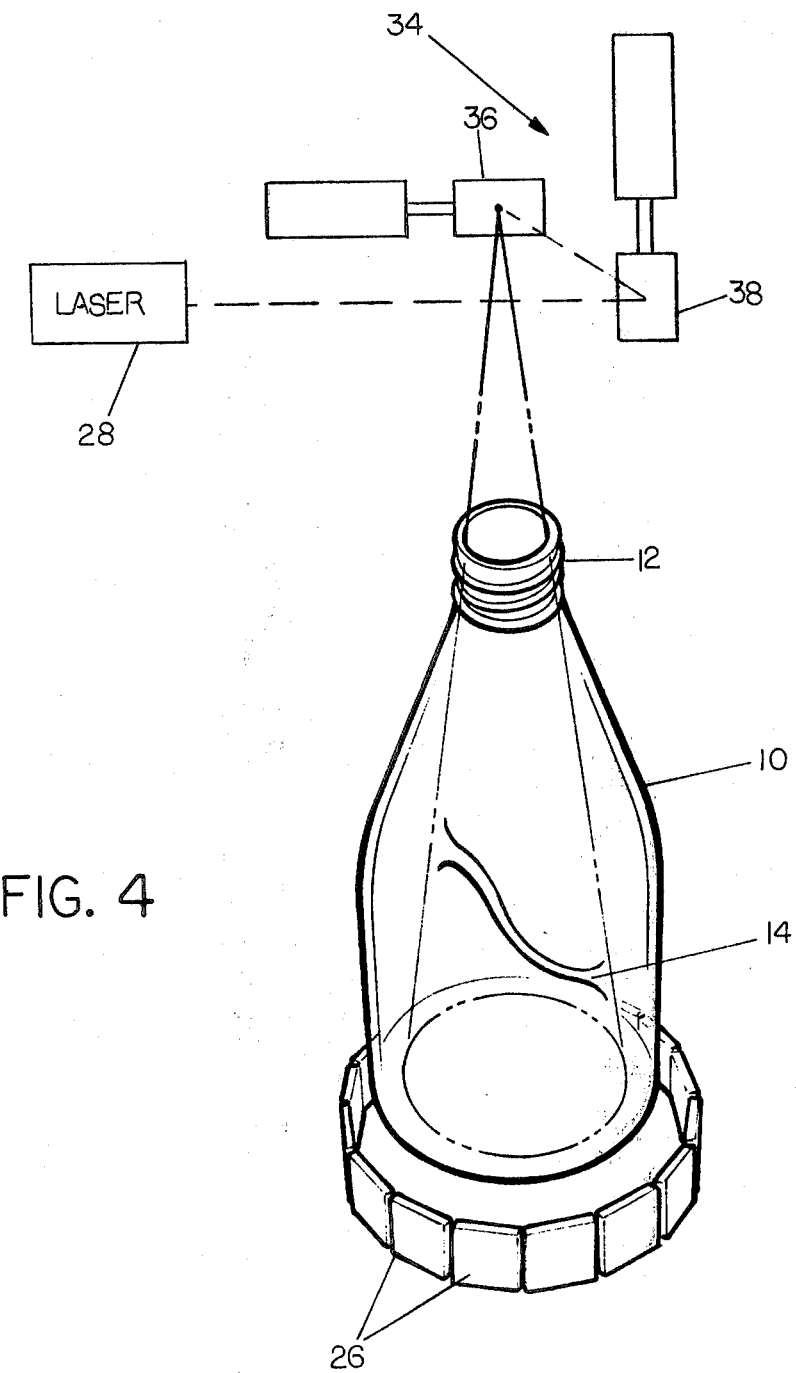
FIG. 4 is a perspective view, similar to FIG. 1, showing an electro-optical scanning system which may be used to inspect a bottle.

Referring now to FIG. 4, an xy electro-optical scanner generally designated 34 may be used to permit inspection of the bottle 10 without requiring rotation of the bottle 10. The scanner 34, which is conventional in the art, consists of a pair of oscillating mirrors 36 and 38, which oscillate 90° out of phase with respect to each other. The scanning rate of the scanner 34 is 2500 Hz, thus making it particularly useful if the inspection device is to be located on a conveyor line. The high scanning rate permits high speed inspection of a series of bottles. The laser beam 30 is reflected from the mirrors 36 and 38 in series thus producing a conical scan, which projects through the finish 12 of the bottle 10. As the laser beam 30 scans the inside of the bottle 10 a scattering pattern will be created whenever a birdswing 14 is encountered. Scattered light is then detected by the circular photocell array 26.

Figure 5:
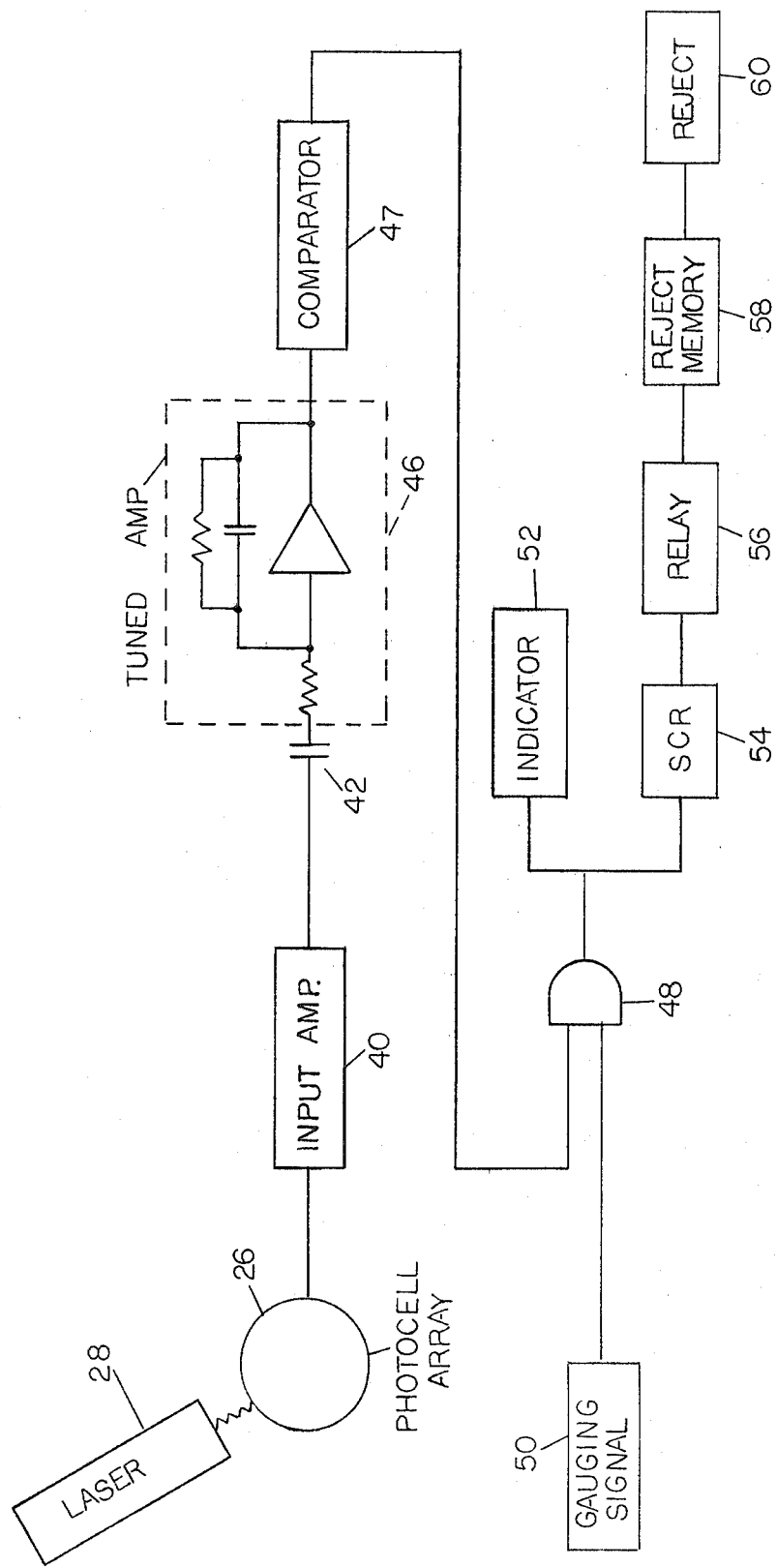
FIG. 5 is a partial block, partial schematic view of a circuit which is used in connection with the detection of birdswings.

Referring to FIG. 5, the output of each of the cells in the photocell array 26 is connected in a parallel fashion to a high speed, high input impedance, FET input amplifier 40, which in the preferred embodiment of the invention is a Teledyne model 1027. The output of the FET amplifier 40 represents the sum of the light which strikes each cell of the photocell array 26. The output of the FET amplifier 40 is connected to an a.c. coupling capacitor 42 which eliminates the d.c. effects of ambient light which strikes the photocell array 26. The capacitor 42 is connected to a tuned amplifier 46, whose output is connected to a comparator 47. The tuned amplifier 46 acts as a high pass active filter and its output is a function of the rate of change of the amount of light striking the photocell array 26. When light from the birdswing 14 strikes the photocell array 26 the output of the tuned amplifier 46 will exceed a predetermined set level of the comparator 47, and an error signal will be generated at the output of the comparator 47. This output is connected to one input of an AND gate 48. A gauging signal 50 is sent to the other input of the AND gate 48 whenever a bottle is in position for inspection. Whenever a gauging signal is present and the comparator 46 is generating an error signal in coincidence, a signal will be provided at the output of the AND gate 48, thus indicating that a birdswing is present in the bottle which is being inspected. The output of the AND gate 48 is connected to an indicator 52 and to an SCR 54. The SCR 54 drives a conventional relay 56 which in turn activates a reject memory 58. After the defective bottle 10 has moved into the correct position, the reject memory 58 causes a rejector 60 to automatically reject the bottle 10. Therefore, whenever a bottle with a birdswing is detected the comparator 47 generates an error signal, the indicator 52 is activated, and the bottle 10 is automatically rejected.

The above described invention is designed to be utilized in conjunction with a machine of the type disclosed in U.S. Pat. No. 3,313,409, issued to J. R. Johnson on Apr. 11, 1967, the disclosure of which is herein incorporated by reference. This type of machine takes glassware from a conveyor and moves it intermittently through several stations on a circular inspection path. At each station, the glassware is inspected for a particular defect or defects. The present invention is designed to operate at one of the inspection stations. If a piece of glassware is determined to be defective, the reject memory 58 will cause the defective piece to be rejected by the rejector after it has completed the inspection cycle and prior to its being returned to the conveyor line.

What is claimed is:

1. Apparatus for inspecting hollow, transparent glass containers having a neck opening for "birdswing" defects comprising:

means for supporting a container on its base at an inspection station;

a light source for generating a beam of light, means mounting said light source such that said light beam passes through the neck opening of said container and impinges on a predetermined portion of the inner sidewall thereof;

means at said inspection station for causing relative movement of said container and said beam of light so that the beam scans the predetermined portion of the inner side wall thereof; and a plurality of photocells adjacent said container and arranged in a circumferential array having a diameter larger than the container beneath said container for detecting light which is scattered outwardly through the wall of said container after impinging on a birdswing, said array being generally coaxial with respect to the vertical axis of said container.

* * * * *